US00PP09321P

United States Patent [19]

deJong

[11] Patent Number: Plant 9,321

[45] Date of Patent: Oct. 10, 1995

[54] POTENTILLA FRUTICOSA 'HINEROB'

[75] Inventor: Gys P. deJong, Lusk, Ireland

[73] Assignee: Hines Nurseries Inc., Irvine, Calif.

[21] Appl. No.: 283,060

[22] Filed: Jul. 29, 1994

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 4,226 3/1978 Barker ..... Plt./54.1

P.P. 4,628 1/1981 Barker ..... Plt./54.1

*Primary Examiner*—James R. Feyrer

*Attorney, Agent, or Firm*—Christie, Parker & Hale

[57] ABSTRACT

A new and distinct variety of *Potentilla fruticosa* named 'Hinerob' bearing orange red flowers.

2 Drawing Sheets

BACKGROUND OF THE INVENTION

*Potentilla fruticosa* are ornamental flowering shrubs which are relatively disease-free and possess varying flower coloration. Potentilla genus is in the rose family and may be an annual or perennial. About five hundred species have been recorded including many varieties of *Potentilla fruticosa*. All Potentilla have five-lobed leaves and flowers, with petals and sepals also in multiples of five. The flowers are attractive on the shrub but do not last well after they are picked.

SUMMARY OF THE INVENTION

This invention relates a new variety of *Potentilla fruticosa* that produces orange red flowers.

The new plant was discovered as a seedling in a controlled planting of the Potentilla variety 'Red Ace' and is believed to be a self seedling of that variety. 'Red Ace' is the subject of U.S. Plant Pat. No. 4,226. The varietal denomination of the new variety is 'Hinerob'. Asexual reproduction of the new variety by cuttings as performed in Lusk County Dublin, Ireland, and Orange County, Calif., has confirmed that the distinguishing characteristics of the new variety are transmitted to succeeding generations.

BRIEF DESCRIPTION OF THE ILLUSTRATIONS

The accompanying photographs show typical specimens of the new variety depicted in color as nearly true as is reasonably possible to make the same in color illustrations of this character.

COMPARISON WITH PARENT

Figure 1:
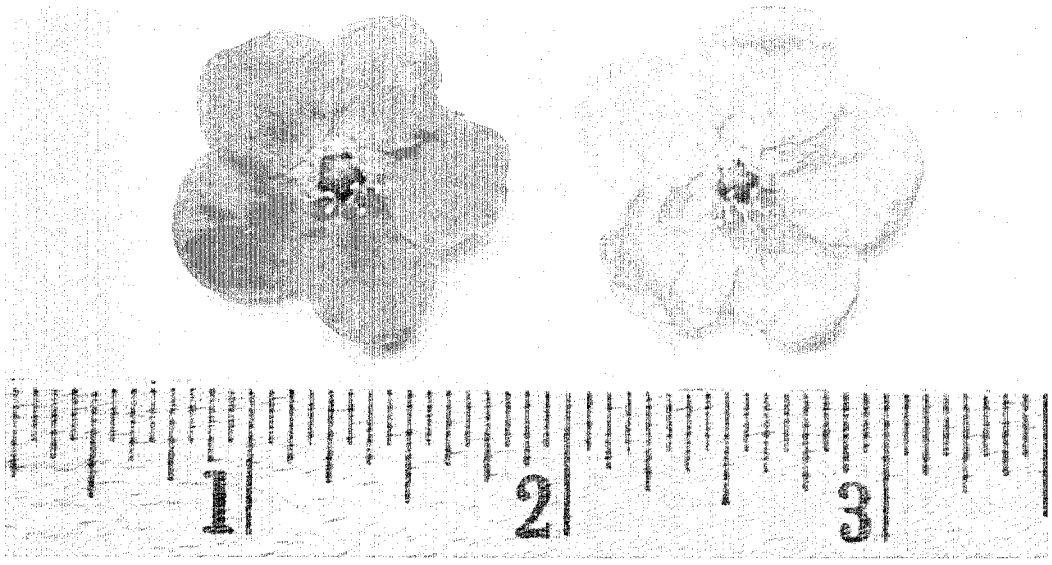
FIG. 1 illustrates the orange red color of the blossom as compared to the yellow orange coloration of the blossoms of the parent variety 'Red Ace'.
Figure 2:
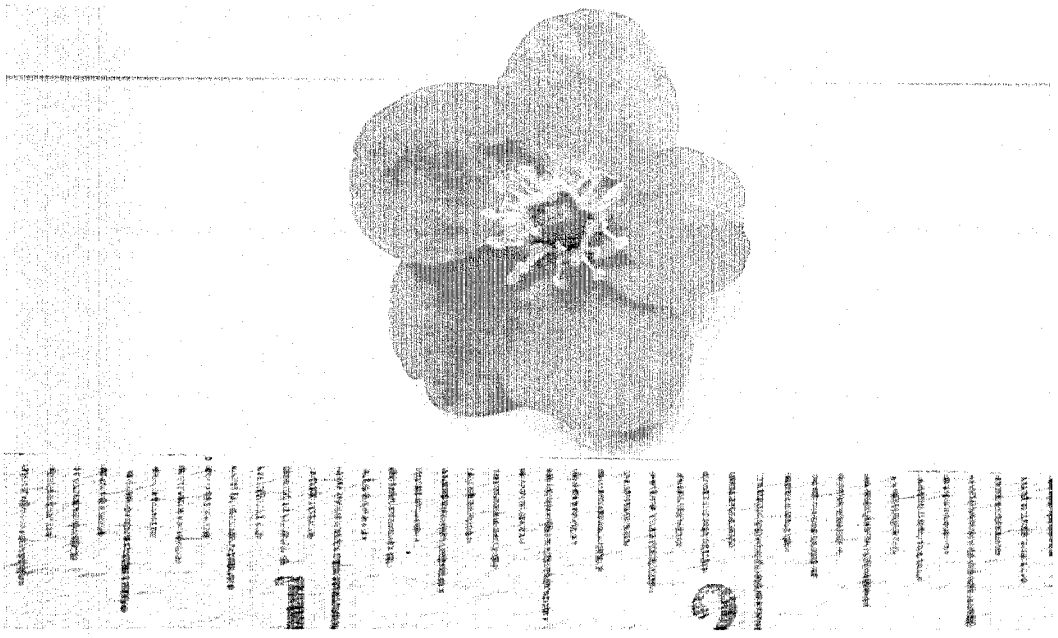
FIG. 2 is a closeup of a flower of the new variety.
Figure 4:
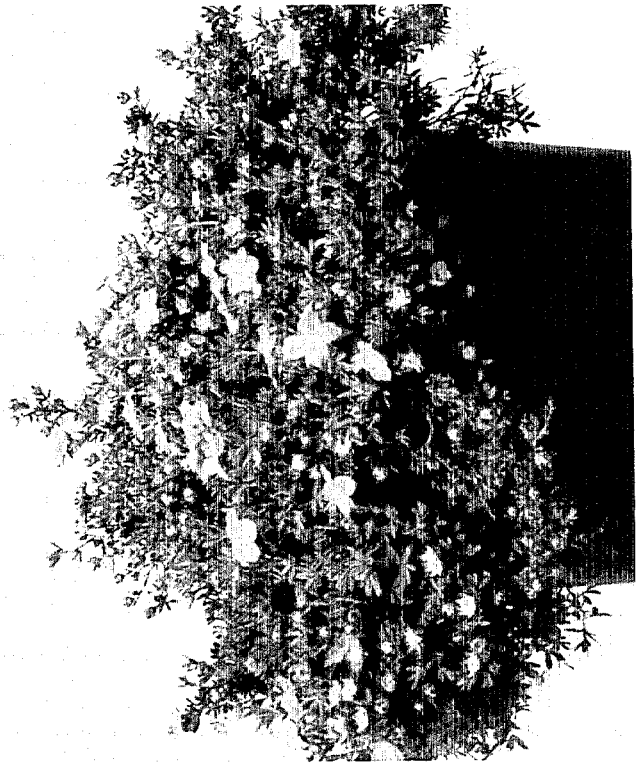
FIGS. 3 and 4 are illustrations of flowering plants of the new variety and of the parent variety, respectively.
Figure 3:
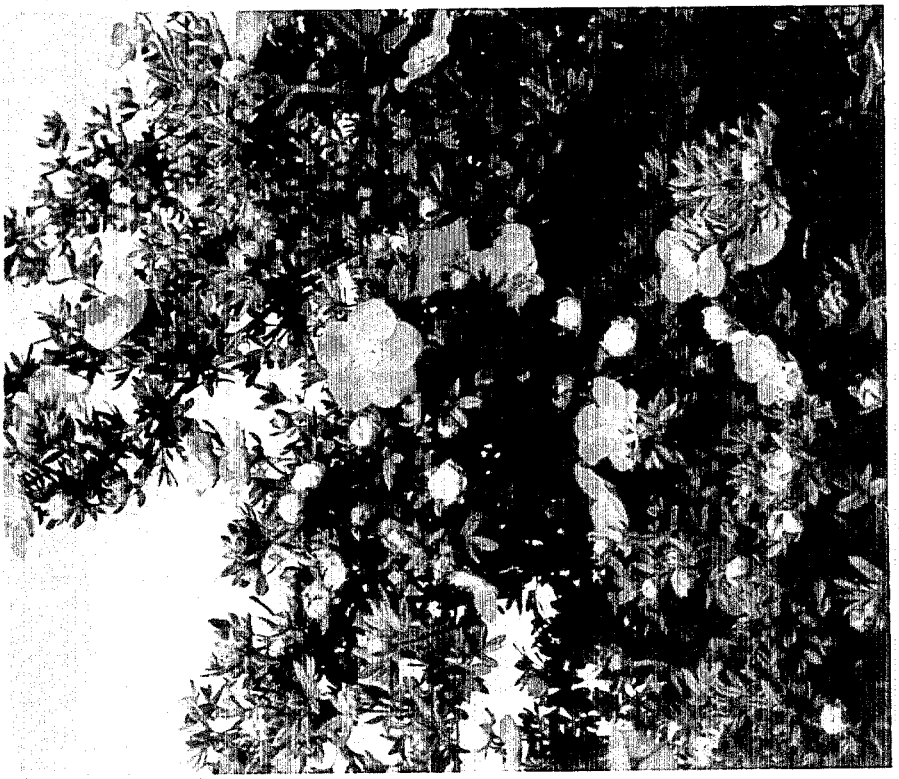

In U.S. Plant Pat. No. 4,226 it is indicated that flowers of 'Red Ace' have red coloration. However, in the Southern California climate although the initial spring flower color of both cultivars display red coloration, the flower color of 'Red Ace' in heat is substantially pure yellow, regardless of irrigation practices. FIG. 1 is a photograph comparing the flowers produced by 'Red Ace' and the new variety in Irvine, Orange County, Calif. taken of flowers on container plants of the same age, on the same day and under the same growing conditions. In similar growing tests in Canada, it has been reported that flowers of both 'Red Ace' and the new variety open red and whereas 'Hinerob' may fade to orange in July and August, 'Red Ace' fades to yellow. Moreover, later produced flowers of 'Hinerob' remain red.

DETAILED DESCRIPTION OF THE NEW VARIETY

The following description was made from established plants grown in containers at Santa Ana, Calif. in from the south of March to June. Color descriptions are provided by reference to The Royal Horticultural Society color chart unless otherwise indicated. Phenotypic expression may vary depending upon environmental, cultural and light conditions.

PLANT

Size: Mature plants are nominally 18"–24" high and 24"–28" wide at full maturity.

Habit: Rounded, densely branched, mounding shrub.

Foliage:

*Leaves.*—Compound of usually five leaflets, palmate, margin — revolute.

*Color of mature leaves.*—The upper surface is near 137C and the under surface is near 138B.

*Size.*—Average leaf width: about 0.9". Average leaf length (Petiole base to leaf apex): about 0.8".

*Shape.*—Oblong, lanceolate.

*Texture.*—Soft.

*Apex.*—Acute.

*Base.*—Cuneate.

*Petioles.*—About 0.1"–0.2".

Hardiness: Hardiness zone 2A, –45° to –50° F.

INFLORESCENCE

Flowers: One or several in a terminal cyme.

*Bloom period.*—March to mid June.

*Form.*—Rounded.

*Arrangement.*—Terminal cyme.

*Petal size.*—Average width: about 0.9 inch. Average length: about 0.8 inch.

*Petal number.*—Normally five.

*Color.*—Near 44A maturing to near 43A. In warm weather conditions, near 30B, maturing to near 26B.

Peduncle: About 0.5 to 0.6 inch.

Fragrance: None.

REPRODUCTIVE SYSTEM

Stamens: Many.
Filaments: About 1/16" with anthers; coloration near 17A–D.
Pistils: Many.
Styles: Very uneven and very loosely separated.
Pollen: Near 17A–D.

Fruit: Achenes.

I claim:

1. A new and distinct variety of *Potentilla Fruticosa* substantially as herein shown and described.

* * * * *

UNITED STATES PATENT AND TRADEMARK OFFICE

CERTIFICATE OF CORRECTION

PATENT NO. : PP 9,321

DATED : October 10, 1995

INVENTOR(S) : Gys P. deJong

It is certified that error appears in the above-indentified patent and that said Letters Patent is hereby corrected as shown below:

Column 2, line 14, change "south" to -- month --.

Signed and Sealed this

Sixteenth Day of April, 1996

Bruce Lehman

*Attest:*

BRUCE LEHMAN

*Attesting Officer*

*Commissioner of Patents and Trademarks*